US012721738B2

(12) United States Patent
Hashimoto et al.

(10) Patent No.: US 12,721,738 B2
(45) Date of Patent: Sep. 1, 2026

(54) PROSTHETIC KNEE JOINT, PROSTHETIC KNEE JOINT POWER GENERATING METHOD, AND TANGIBLE COMPUTER-READABLE STORAGE MEDIUM STORING PROGRAM

(71) Applicant: NABTESCO CORPORATION, Tokyo (JP)

(72) Inventors: Hiroaki Hashimoto, Tokyo (JP); Shingo Miwa, Tokyo (JP)

(73) Assignee: NABTESCO CORPORATION, Tokyo (JP)

( * ) Notice: Subject to any disclaimer, the term of this patent is extended or adjusted under 35 U.S.C. 154(b) by 1087 days.

(21) Appl. No.: 17/679,739

(22) Filed: Feb. 24, 2022

(65) Prior Publication Data

US 2022/0339010 A1 Oct. 27, 2022

(30) Foreign Application Priority Data

Apr. 21, 2021 (JP) ................................ 2021-071956

(51) Int. Cl.
*A61F 2/64* (2006.01)
*A61F 2/68* (2006.01)
*A61F 2/74* (2006.01)
*A61F 2/30* (2006.01)

(52) U.S. Cl.
CPC ................ *A61F 2/64* (2013.01); *A61F 2/744* (2021.08); *A61F 2002/6827* (2013.01)

(58) Field of Classification Search
CPC ....... A61F 2/74; A61F 2/741; A61F 2002/708
See application file for complete search history.

(56) References Cited

U.S. PATENT DOCUMENTS

2007/0233279 A1 10/2007 Kazerooni et al.
2010/0023133 A1 1/2010 Fairbanks et al.
2012/0226364 A1 9/2012 Kampas et al.
2015/0164660 A1* 6/2015 Will ...................... A61F 5/0123 602/26
2015/0202057 A1 7/2015 Zahedi et al.

FOREIGN PATENT DOCUMENTS

DE 102008045113 A1 * 3/2010 ............... A61F 2/70
DE 102008045113 B4 8/2011
EP 2331026 B1 11/2018
JP 2013-510605 A 3/2013
JP 2015-521505 A 7/2015

OTHER PUBLICATIONS

Translation of DE102008045113B4 (Year: 2008).*
Extended European Search Report dated Sep. 6, 2022, issued in corresponding European Patent Application No. 22159971.5 (11 pgs.).
Notice of Reasons for Rejection dated Aug. 13, 2024, issued in corresponding Japanese Patent Application No. 2021-071956 with English translation (10 pgs.).
Office Action dated Jun. 2, 2026, issued in corresponding European Patent Application No. 22159971.5 (8 pgs.).

* cited by examiner

*Primary Examiner* — Christie Bahena
(74) *Attorney, Agent, or Firm* — Pillsbury Winthrop Shaw Pittman, LLP

(57) ABSTRACT

A prosthetic knee joint includes a thigh connection part to be positioned near a thigh part, a lower leg part rotatably coupled to the thigh connection part, and a power generating, part for generating power using a resistance resulting from rotation of the lower leg part relative to the thigh connection part.

11 Claims, 11 Drawing Sheets

PROSTHETIC KNEE JOINT, PROSTHETIC KNEE JOINT POWER GENERATING METHOD, AND TANGIBLE COMPUTER-READABLE STORAGE MEDIUM STORING PROGRAM

CROSS-REFERENCE TO RELATED APPLICATIONS

This application is based on and claims the benefit of priority from Japanese Patent Application Serial No. 2021-071956 (filed on Apr. 21, 2021), the contents of which are hereby incorporated by reference in their entirety.

TECHNICAL FIELD

The present invention relates to a prosthetic knee joint for generating power through movement of a body, a prosthetic knee joint power generating method, and a tangible computer-readable storage medium storing a program.

BACKGROUND

Japanese Patent Application Publication No. 2013-510605 ("the 605 Publication") discloses a prosthetic device (a lower extremity prosthesis) including a thigh shaft, a lower leg shaft, a prosthetic foot, a joint and a connection part. In the prosthetic device disclosed in the '605 Publication, a moment sensor is provided on the joint to determine the effective knee moment, and resistance units are provided on the lower leg shaft to provide bending and stretching resistances. The resistance units are controlled based on sensor data and results of evaluating the sensor data.

Inside such a lower extremity prosthesis, a power source is provided to feed power to the sensor and control device, so that a hydraulic device and other internal devices are controlled. Therefore, the lower extremity prosthesis equipped with such internal devices needs to be recharged at a predetermined timing or once the power is used up. United States Patent Application Publication No. 2015/0202057 ("the '057 Publication") discloses a technology of generating power through bending of a prosthetic leg and charging a storage battery with the generated power.

As for lower extremity prostheses with power generation devices, the power generation devices preferably do not impair the intended function of the prostheses when users use the prostheses and do not impede the comfort of the users when the users are walking. According to the technology disclosed in the '057 Publication, bending generates power to recharge the storage battery, and the stored power is used to perform stretching. This may limit the pattern of the power generation.

SUMMARY

The present invention is made in light of the above circumstances, and, provides a prosthetic knee joint that is capable of using a resistance produced by movement of the prosthetic knee joint to obtain regenerative power.

The present invention provides a prosthetic knee joint including a thigh connection part positioned near a thigh part, a lower leg, part rotatably coupled to the thigh connection part, and a power generating part for generating power using a resistance resulting from rotation of the lower leg part relative to the thigh connection part.

According to the present invention, the prosthetic knee joint may include a fluid circuit through which a working fluid flows, where the fluid circuit is configured to generate the resistance, and the power generating unit may generate power through the flowing of the working fluid.

According to the present invention, the power generating unit may include a gear motor configured to be driven by the working fluid, to generate power.

According to the present invention, the fluid circuit may include a control valve for adjusting the resistance by controlling the flowing of the working fluid.

According to the present invention, the prosthetic knee joint may include a control unit for controlling operation of the control valve, where the control unit is configured to operate with the power generated by the power generating unit.

According to the present invention, the fluid circuit may include a hydraulic cylinder configured to operate with the working fluid, and a power generation flow channel connecting together a first port and a second port defined within the hydraulic cylinder and partitioned by a piston movable within the hydraulic cylinder, where the power generation flow channel has the power generating unit in a middle thereof.

According to the present invention, the control valve may be provided in the power generation flow channel and configured to control a relation between (i) a flow rate of the working fluid flowing through the power generation flow channel and (ii) differential pressure caused by pressure loss.

According to the present invention, the power generation flow channel may include a different flow channel connecting together the first and second ports, and the different flow channel may have a different control valve for controlling a relation between a flow rate of the working fluid flowing therethrough and differential pressure caused by pressure loss.

According to the present invention, the power generation flow channel may include a first parallel flow channel through which the working fluid flows from the first port to the second port, where the first parallel flow channel has a first parallel control valve for adjusting a flow rate of the working fluid, and a second parallel flow channel through which the working fluid flows from the second port to the first port, where the second parallel flow channel has a second parallel control valve for adjusting a flow rate of the working fluid, and the control unit may control the first and second parallel control valves independently, to adjust the flow rate of the working fluid in a flow direction toward the power generating unit.

According to the present invention, the prosthetic knee joint may include a first check valve for restricting the working fluid from flowing from the second port to the first port in the first parallel flow channel, and a second check valve for restricting the working fluid from flowing from the first port to the second port in the second parallel flow channel.

According to the present invention, the power generation flow channel may have a first flow channel connecting together the first port and one end of an intermediate flow channel having the power generating unit in a middle thereof, a second flow channel connecting together the second port and the one end of the intermediate flow channel, a third flow channel connecting together the first port and the other end of the intermediate flow channel, and a fourth flow channel connecting together the second port and the other end of the intermediate flow channel. The first flow channel may have a first control valve for adjusting the flow rate of the working fluid, the second flow channel may have a second control valve for adjusting the flow rate of the working fluid, the third flow channel may have a third check valve for restricting the working fluid from flowing in a direction from the first port to the intermediate flow channel and allowing the working fluid to flow in a direction from the intermediate flow channel to the first port, and the fourth flow channel may have a fourth check valve for restricting the working fluid from flowing in a direction from the second port to the intermediate flow channel and allowing the working fluid to flow in a direction from the intermediate flow channel to the second port.

According to the present invention, the power generation flow channel may include first and second flow channels parallel to each other and connecting together the second port and one end of an intermediate flow channel having the power generating unit in a middle thereof, and third and fourth flow channels parallel to each other and connecting together the first port and the other end of the intermediate flow channel. The first flow channel may have a first control valve for adjusting the flow rate of the working fluid, the third flow channel may have a second control valve for adjusting the flow rate of the working fluid, the second flow channel may have a third check valve for allowing the working fluid to flow from the intermediate flow channel to the second port and restricting the working fluid from flowing from the second port to the intermediate flow channel, and the fourth flow channel may have a fourth check valve for allowing the working fluid to flow from the intermediate flow channel to the first port and restricting the working fluid from flowing from the first port to the intermediate flow channel.

According to the present invention, the prosthetic knee joint may include a bypass flow channel connecting together the one end and the other end of the intermediate flow channel, and a bypass control or relief valve provided in the bypass flow channel, where the bypass control or relief valve is configured to adjust the flow rate of the working fluid flowing through the bypass flow channel.

According to the present invention, the prosthetic knee joint may include a control unit for controlling operation of the control valve, where the control unit is configured to operate with the power generated by the power generating unit, and the control unit may adjust the different control valve in an appropriate manner to generate a resistance weaker than a power generation resistance generated by the power generating unit and adjust the control valve in an appropriate manner to generate a resistance stronger than the power generation resistance.

One aspect of the present invention provides a prosthetic knee joint including a thigh connection part to be positioned near a thigh part, a lower leg part rotatably coupled to the thigh connection part, a power generating unit for generating power using a resistance resulting from rotation of the lower leg part relative to the thigh connection part, a fluid circuit through which a working fluid flows, where the fluid circuit has the power generating unit, and the fluid circuit is configured to generate the resistance, a control valve provided in the fluid circuit, where the control valve is configured to adjust the resistance by controlling the flowing of the working fluid, a control unit for controlling operation of the control valve, where the control unit is configured to operate with the power generated by the power generating unit a hydraulic cylinder provided in the fluid circuit, where the hydraulic cylinder is configured to be operated by the working fluid, and a power generation flow channel connecting together a first port and a second port defined within the hydraulic cylinder and partitioned by a piston movable within the hydraulic cylinder, where the power generation flow channel has the power generating unit in a middle thereof. The power generation flow channel has a first flow channel connecting together the first port and one end of an intermediate flow channel having the power generating unit in a middle thereof, a second flow channel connecting together the second port and the one end of the intermediate flow channel, a third flow channel connecting together the first port and the other end of the intermediate flow channel, and a fourth flow channel connecting together the second port and the other end of the intermediate flow channel. The first flow channel has a first control valve for adjusting a flow rate of the working fluid. The second flow channel has a second control valve for adjusting the flow rate of the working fluid. The third flow channel has a third, check valve for restricting the working fluid from flowing in a direction from the first port to the intermediate flow channel and allowing the working fluid to flow in a direction from the intermediate flow channel to the first port. The fourth flow channel has a fourth check valve for restricting the working fluid from flowing in a direction from the second port to the intermediate flow channel and allowing the working fluid to flow in a direction from the intermediate flow channel to the second port.

One aspect of the present invention provides a prosthetic knee joint including a thigh connection, part to be positioned near a thigh part, a lower leg part rotatably coupled to the thigh connection part, a power generating unit for generating power using a resistance resulting from rotation of the lower leg part relative to the thigh connection part, a fluid circuit through which a working fluid flows, where the fluid circuit has the power generating unit, and the fluid circuit is configured to generate the resistance, a control valve provided in the fluid circuit, where the control valve is configured to adjust the resistance by controlling the flowing of the working fluid, a control unit for controlling operation of the control valve, where the control unit is configured to operate with the power generated by the power generating unit, a hydraulic cylinder provided in the fluid circuit, where the hydraulic cylinder is configured to be operated by the working fluid, and a power generation flow channel connecting together a first port and a second port defined within the hydraulic cylinder and partitioned by a piston movable within the hydraulic cylinder, where the power generation flow channel has the power generating unit in a middle thereof. The power generation flow channel includes first and second flow channels parallel to each other and connecting together the second port and one end of an intermediate flow channel having the power generating unit in a middle thereof, third and fourth flow channels parallel to each other and connecting together the first port and the other end of the intermediate flow channel and a bypass flow channel connecting together the one end and the other end of the intermediate flow channel. The first flow channel has a first control valve for adjusting a flow rate of the working fluid. The third flow channel has a second control valve for adjusting the flow rate of the working fluid. The second flow channel has a third check valve for allowing the working fluid to flow from the intermediate flow channel to the second port and restricting the working fluid from flowing from the second port to the intermediate flow channel. The fourth flow channel has a fourth check valve for allowing the working fluid to flow from the intermediate flow channel to the first port and restricting the working fluid from flowing from the first port to the intermediate flow channel. The bypass flow channel has a bypass control or relief valve for adjusting the flow rate of the working fluid, flowing through the bypass flow channel.

One aspect of the present invention provides a prosthetic knee joint power generating method for use in a prosthetic knee joint including a thigh connection part to be positioned near a thigh part, and a lower leg part rotatably coupled to the thigh connection part. Power is generated using a resistance resulting from rotation of the lower leg part relative to the thigh connection part.

One aspect of the present invention provides a tangible computer-readable storage medium storing a program for generating power, in a prosthetic knee joint including a thigh connection part to be positioned near a thigh part, and a lower leg part rotatably coupled to the thigh connection part, while causing a control device to control a value of a resistance resulting from rotation of the lower leg part relative to the thigh connection part.

Advantageous Effects

According to one or more of the aspects of the invention, the resistance produced by movement of the prosthetic knee joint can be used to obtain regenerative power.

DESCRIPTION OF THE PREFERRED EMBODIMENTS

The following describes the basic configuration of prosthetic knee joints relating to embodiments of the present invention.

Figure 1:
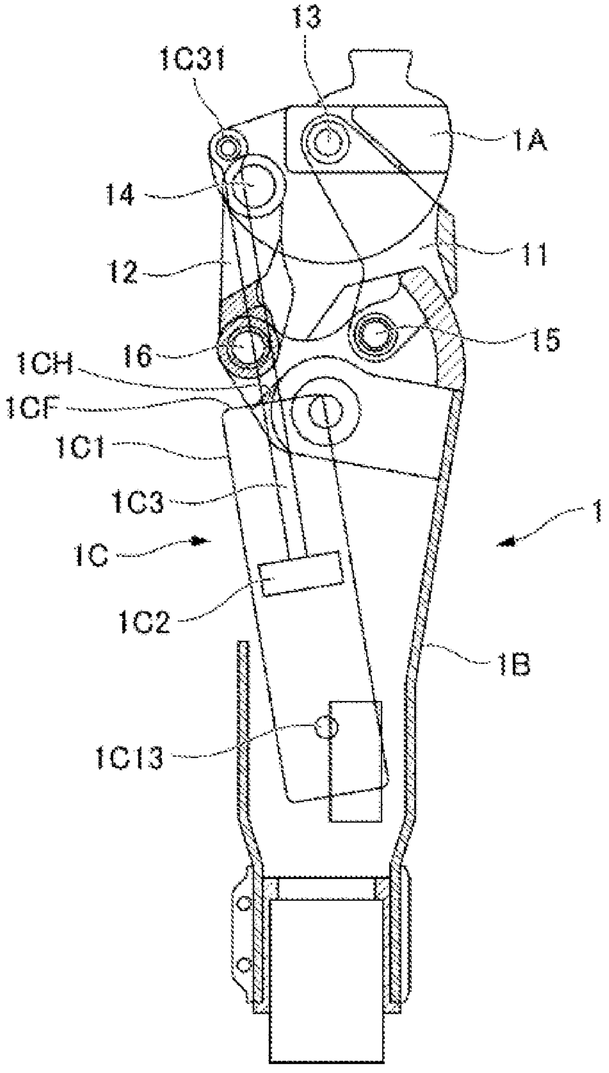
FIG. 1 is a sectional view showing the configuration of a prosthetic knee joint according to an embodiment of the invention.

As shown in FIG. 1, a prosthetic knee joint 1 is a device configured to replace the thigh and lower part of the body of a user (the wearer of the prosthetic knee joint 1). The prosthetic knee joint 1 includes a thigh connection part 1A connectable to the thigh, a lower leg part 1B rotatably coupled to the thigh connection part 1A, and a cylinder 1C (hydraulic cylinder) coupled to the thigh connection part 1A and the lower leg part 1B. A front link part 11 is rotatably coupled between and lies on the front side of the thigh connection part 1A and the lower leg part 1B. A rear link part 12 is rotatably coupled between and lies on the rear side of the thigh connection part 1A and the lower leg part 1B. The prosthetic knee joint 1 is controlled by a control device 10 (see FIG. 3), which will be described later. The control device 10 is provided within the prosthetic knee joint 1 at any desired position.

The upper portion of the front link part 11 is rotatably coupled with the thigh connection part 1A via a first shaft 13. The lower portion of the front link part 11 is rotatably coupled with the lower leg part 1B via a third shaft 15. The upper portion of the rear link part 12 is rotatably coupled to the thigh connection part 1A via a second shaft 14. The lower portion of the rear link part 12 is rotatably coupled with the lower leg part 1B via a fourth shaft 16.

The thigh connection part 1A is connectable to a socket (e.g., see Japanese Patent Application Publication No. 2017-6339 ("the '339 Publication"), FIG. 1) configured to receive the lower edge of the thigh of the user. With the above arrangement, the lower leg part 1B constitutes a rotatable mechanism with the front and rear link parts 11 and 12 corresponding to the axis of the knee, and is rotatable relative to the thigh connection part 1A. In other words, the thigh connection part 1A, the lower leg part 1B, the front link part 11, and the rear link part 12 constitute a four section link. This means that the lower leg part 1B is rotatable around the axis of the knee (an imaginary axis) relative to the thigh connection part 1A, as described above.

The rotation of the thigh connection part 1A and the lower leg part 1B is restricted or assisted by a cylinder 1C (hydraulic cylinder) that is extendable and contractable. The cylinder 1C is positioned correspondingly to the inflated tibia. The upper end of the cylinder 1C is rotatably coupled to the thigh connection part 1A. The lower end of the cylinder 1C is rotably coupled with the lower leg part 1B. The cylinder 1C includes a cylinder tube 1C1, a piston 1C2, and a piston rod 1C3. The cylinder tube 1C1 substantially stands upright, the piston 1C2 is movable within the cylinder tube 1C1, and the piston rod 1C3 is coupled to the upper end of the piston 1C2. The cylinder 1C may be provided on the thigh connection part 1A.

The cylinder tube 1C1 is bottomed and shaped like a circular cylinder. The upper end of the cylinder tube 1C1 is closed by a lid 1CF. The lid 1CF has a through hole 1CH formed therein at the center thereof. The piston rod 1C3 is inserted through the through hole. The lower end of the cylinder tube 1C1 is rotatably coupled with the lower leg part 1B via a coupling part 1C13. The inner space within the cylinder tube 1C1 is partitioned by the piston 1C2 shaped like a circular plate. The piston 1C2 has an outer shape slightly smaller than the inner diameter of the cylinder tube 1C1, for example. The cylinder tube 1C1 may be shaped differently than a circular cylinder.

The upper surface of the piston 1C2 is coupled with the lower end of the piston rod 1C3. The piston rod 1C3 is shaped like a circular cylinder. The piston rod 1C3 partially projects out of the cylinder tube 1C1 through the through hole 1CH. The upper end of the piston rod 1C3 is rotatably coupled to the thigh connection part 1A via a coupling part 1C31.

In the prosthetic knee joint 1 having the above arrangement, the lower leg part 1B rotates relative to the thigh connection part 1A, and the rotation results in the piston rod 1C3 extending and contracting relative to the cylinder tube 1C1. The extension and contraction of the piston rod 1C3 causes the piston 1C2 to move within the cylinder tube 1C1, and this generates a resistance. In this way, the cylinder 1C provides a resistance when the lower leg part 1B rotates relative to the thigh connection part 1A.

Figure 2:
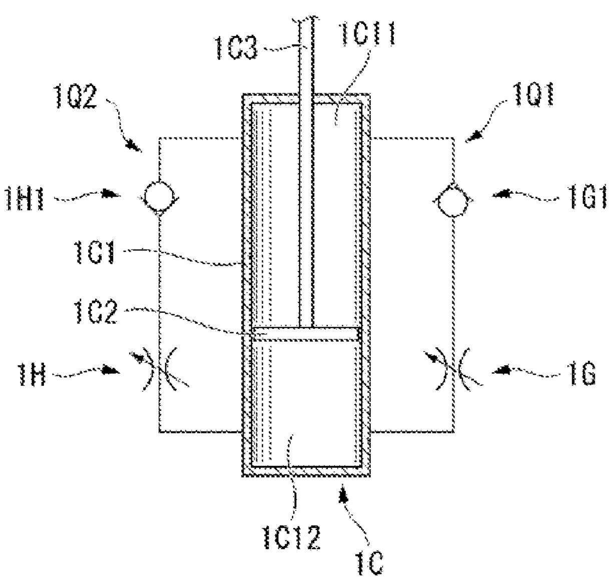
FIG. 2 schematically shows the configuration of a cylinder of the prosthetic knee joint.

As shown in FIG. 2, the cylinder 1C has a fluid circuit provided therein for controlling the resistance. The inner space within the cylinder tube 1C1 is partitioned by the piston 1C2 In the cylinder tube 1C1, the piston 1C2 serves as a partition and defines a first port 1C11 and a second port 1C12. The first port 1C11 is positioned on the side including the piston rod 1C3 with respect to the piston 1C2, and the second port 1C12 is positioned opposite the piston rod 1C3 with respect to the piston 1C2.

The cylinder tube 1C1 is filled with a working fluid. The working fluid is, for example, a hydraulic oil The working fluid may be a fluid of a different type than a hydraulic oil The first port 1C11 and the second port 1C12 are in communication with each other through a flow channel 1Q1—through which the working fluid flows. In the flow channel 1Q1, a stretching-side valve 1G, (also known as a first parallel control valve), and a stretching-side check valve 1G1 are connected in series. The stretching-side valve 1G and check valve 1G1 maybe connected in a reversed order. The first and second port C11 and 1C12 are connected to each other also through a flow channel 1Q2 through which the working fluid flows. In the flow channel 1Q2, a bending-side valve 1H, (also known as a second parallel control valve), and a bending-side check valve 1H1 are connected in series. The bending-side valve 1H and the check valve 1H1 may be connected in a reversed order.

Figure 3:
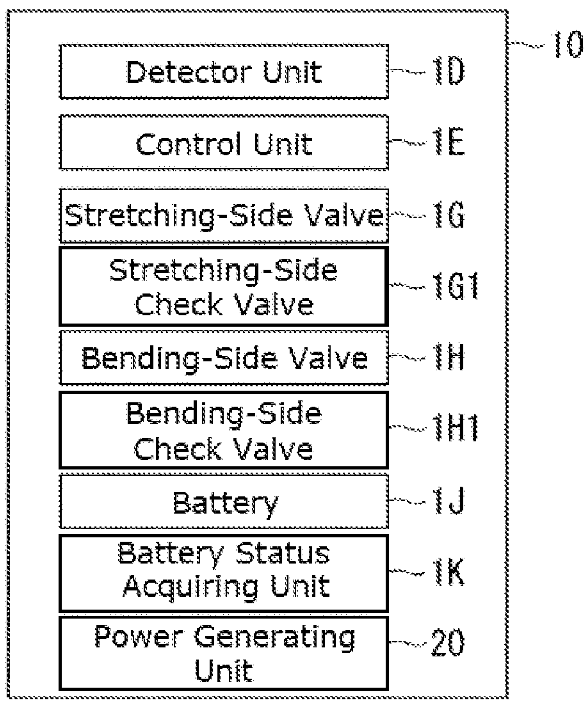
FIG. 3 is a block diagram showing the configuration of a control device for controlling the prosthetic knee joint.

FIG. 3 shows the configuration of a control device 10 for controlling the prosthetic knee joint 1. The control device 10 includes, for example, a detector unit 1D, a control unit 1E, the stretching-side valve 1G, the stretching-side check valve 1G1 the bending-side valve 1H, the bending-side check valve 1H1, a battery 1J, a battery status acquiring unit 1K and a power generating unit 20. The power generating unit 20 will be described below.

The detector unit 11D directly or indirectly obtains information about the posture of the prosthetic knee joint 1, the load applied to the prosthetic knee joint 1, and how the thigh connection part 1A and the lower leg part 1B are relatively positioned. The detector unit 1D obtains information about the posture of the prosthetic knee joint 1, the load applied to the prosthetic knee joint 1, and how the thigh connection part 1A and the lower leg part 1B are relatively positioned by having a load sensor, a six-axis inertial sensor and a knee angle sensor disclosed in, for example, the '339 Publication in FIG. 2. According to other examples, the detector unit 1D may obtain information about how the thigh connection part 1A and the lower leg part 1B are relatively positioned by, for example, measuring the distance in a manner done by a position detection unit disclosed in Japanese Patent Application Publication No. 2019-180887 ("the '887 Publication") in FIG. 2, and may obtain information about the posture of the prosthetic knee joint 1, the load applied to the prosthetic knee joint 1, and how the thigh connection part 1A and the lower leg part 1B are relatively positioned, by, for example, measuring the tilt angle in a manner done by a position detection unit disclosed in the '887 Publication in FIG. 6.

The control unit 1E, controls the resistance of the cylinder 1C based on the result detected by the detector unit 1D. The control unit 1E estimates the state of the user's movement based on the result detected by, the detector unit 1D. In other words, the control unit 1E controls the resistance of the cylinder 1C such that the produced resistance corresponds to the state of the user's movement. The control unit 1E operates with the power generated by the power generating unit 20. In order to stabilize the power fed, thereto, the control unit 1E charges the battery 1J with the power generated by the power generating unit 20 and operates with the power stored in the battery 1J.

The stretching-side valve 1G adjusts the volume of the working fluid flowing through the flow channel 1Q1 to restrict the extension of the cylinder 1C. Adjusting the stretching-side valve 1G regulates the flow of the working fluid from the first port 1C11 to the second port 1C12. This restricts the stretching of the prosthetic knee joint 1. The opening of the stretching-side valve 1G is controlled by the control unit 1E. As the opening of the stretching-side valve 1G decreases, this makes it difficult for the working fluid in the first port 1C11 in the cylinder tube 1C1 to flow into the second port 1C12 through the stretching-side valve 1G.

In other words, when the opening of the stretching-side valve 1G is reduced, this prevents the cylinder 1C from extending, thereby preventing the prosthetic knee joint 1 from being stretched. Accordingly, when it is required to restrict the stretching, of the prosthetic knee joint 1, the control unit 1E reduces the opening of the stretching-side valve 1G. The stretching-side check valve 1G1 prevents the fluid in the second port 1C12 from flowing back into the first port 1C11 through the stretching-side valve 1G when the stretching-side valve 1G is opened.

The bending-side valve 1H adjusts the volume of the working fluid flowing, through the flow channel 1Q2 to restrict the contraction of the cylinder 1C. Adjusting, the bending-side valve 1H regulates the flow of the working fluid from the second port 1C12 to the first port 1C11. This restricts the bending of the prosthetic knee joint 1. The opening of the bending-side valve 1H is controlled by the control unit 1E. As the opening of the bending-side valve 1H is reduced, this makes it difficult for the fluid in the second port 1C12 in the cylinder tube 1C1 to flow into the first port 1C11 through the bending-side valve 1H.

In other words, when the opening of the bending-side valve 1H is reduced, this prevents the cylinder 1C from contracting, thereby preventing the prosthetic knee joint 1 from bending. Accordingly, when it is required to restrict the bending of the prosthetic knee joint 1, the control unit 1E reduces the opening of the bending-side valve 1H. The bending-side check valve 1H1 prevents the fluid in the first port 1C11 from flowing back into the second port 1C12 through the bending-side valve 1H when the bending-side valve 1H is opened.

The control unit 1E performs various types of arithmetic and logical operations based on the results detected by the detector unit 1D. The battery 1J feeds power to the constituents making up the prosthetic knee joint 1 (in detail, the parts that consume power when operated), such as the detector unit 1D and the control unit 1E. The battery status acquiring unit 1K acquires indication of the status of the battery 1J (e.g., data indicating the charge rate (SOC) (remaining power), the capacity, the open circuit voltage, the open circuit potential, etc.). The battery 1J stores the power generated by the power generating unit 20. The amount of the power stored in the battery 1J is controlled by the control unit 1E based on the data acquired by the battery status acquiring unit 1K, so that overloading and overdischarging is prevented. The battery 1J is constituted by a secondary battery, for example. The battery 1J may be constituted by a capacitor.

The control unit 1E estimates the state of the user's movement based on the results detected by the detector unit 1D, more specifically, estimates whether the user is walking or not. Furthermore, if the user is walking, the control unit 1E estimates which one of the phases of the walking (the bending period during the swing phase, the stretching period during the swing phase, the stance phase, and the like) the user is placed in. When the user is walking and placed in the bending period during the swing phase, the control unit 1E lowers the bending resistance. On the other hand, when the user is placed in the stance phase, the control unit 1E increases the bending resistance. When estimating that the user is not walking, the control unit 1E places the prosthetic knee joint 1 in, for example, a maximum bending mode, a bicycle free mode, a seating free mode, a safety lock mode, a standing still mode, or the like.

The above embodiment may be worked without the flow channels 1Q1 and 1Q2. In this case, the control unit 1F may adjust a power generation resistance of the power generating unit 20 in order to adjust the flow rate of the working fluid flowing through a flow channel 1Q3 during bending or stretching. Stated differently, the control unit 1E may adjust the power generation resistance generated between the terminals of a gear motor provided in the power generating unit 20 or the duration of conduction through the gear motor based on, for example, pulse width modulation (PWM), thereby changing the rotation resistance of the gear motor.

As described above, the prosthetic knee joint 1 can generate power using the resistance resulting from bending or stretching, so that the regenerative power can be used as the power source for the prosthetic knee joint 1. The prosthetic knee joint 1 can generate power using the energy of the working fluid flowing through the fluid circuit, which generates a resistance through bending or stretching of the prosthetic knee joint 1.

First Embodiment

Figure 4:
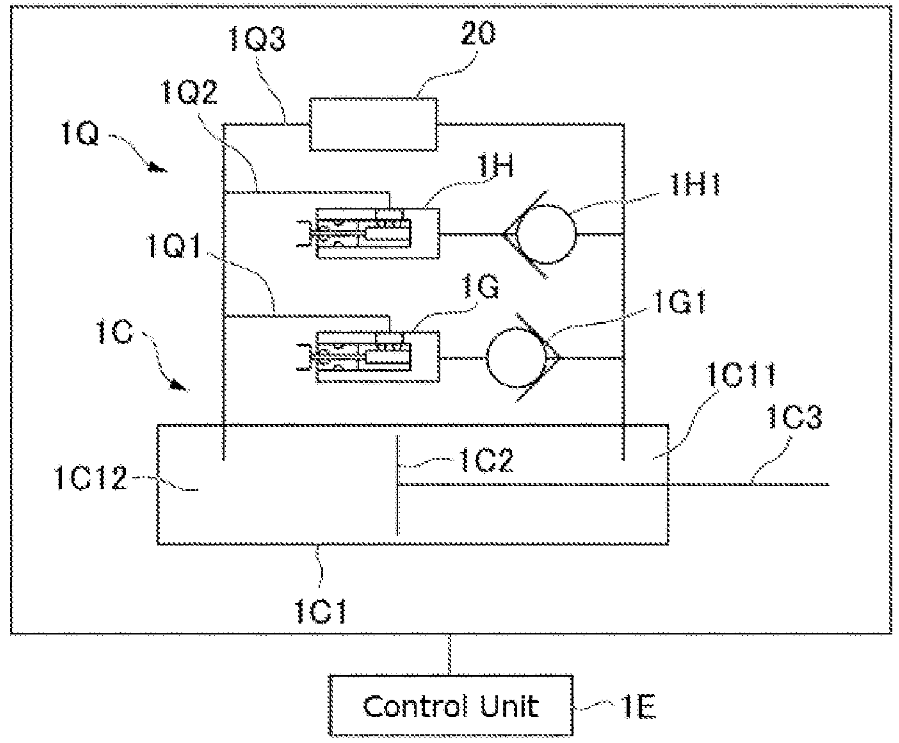
FIG. 4 schematically shows the configuration of a hydraulic circuit of the cylinder including a power generating unit.

The following describes the power generating unit 20 of the prosthetic knee joint 1. As shown in FIG. 4, the power generating unit 20 is provided in the cylinder 1C in the prosthetic knee joint 1. The power generating unit 20 generates power using the resistance generated through either bending or extending of the knee joint of the body. The power generating unit 20 generates power using, for example, a resistance resulting from rotation of the thigh connection part 1A and the lower leg part 11 around the axis of the knee where the thigh connection part 1A and the lower leg part 113 are rotatably coupled together. In the example shown in FIG. 4, the power generating unit 20 is configured to generate power through bending, during which the cylinder 1C contract, and to generate power through stretching, during which the cylinder 1C extends.

The cylinder 1C has a fluid circuit 1Q (hydraulic circuit) through which a working fluid flows. The fluid circuit 1Q experiences a differential pressure caused by a loss in pressure of the working fluid, which results in a resistance generated in the cylinder 1C. The working fluid experiences a resistance resulting from a differential pressure caused by pressure loss between the pressure in the flow channel connected to one side of the power generating unit 20 and the pressure in the flow channel connected to the other side. The resistance force generated in the fluid circuit 1Q is calculated by multiplying this differential pressure by the area of the piston 1C2.

The fluid circuit 1Q includes the cylinder 1C configured to operate with the working fluid, the flow channel 1Q3 (a power generation flow channel), and other flow channels. The flow channel 1Q3 connects together the first and second ports 1C11 and 1C12 defined in the cylinder 1C and partitioned by the piston 1C2, which is movable within the cylinder 1C, and has the power generating, unit 20 in the middle thereof. The other channels include, for example the flow channel 1Q1 (a first parallel flow channel) and the flow channel 1Q2 (the second parallel flow channel). The flow channel 1Q3 connects together the first and second ports 1C11 and 1C12. In the fluid circuit 1Q, the other flow channels than the flow channel 1Q3, more specifically, the flow channels 1Q1 and 1Q2 are arranged parallel. With the flow channels 1Q1 and 1Q2 being provided, power can be generated using the resistance resulting from stretching or bending.

When the piston rod 1C3 extends, the working fluid is discharged from the first port 1C11, flows through the flow channels 1Q3 and 1Q1, and flows into the second port 1C12. When the piston rod 1C3 contracts, the working fluid is discharged from the second, port 1C12, flows through the flow channels 1Q3 and 1Q2, and flows into the first port 1C11. The flow channels 1Q1 and 1Q2 are bypass flow channels running parallel to the flow channel 1Q3. The flow channel 1Q1 has a control valve (the stretching-side valve 1G) connected thereto, which will be described below. The flow channel 1Q2 has a control valve (the bending-side valve 1H) connected thereto, which will be described below. The power, generating unit 20 generates power using the working fluid flowing through the flow channel 1Q3. The resistance used in the power generating unit 20 is adjusted by changing the opening of the stretching- or bending-side valve 1G or 1H.

The power generating unit 20 is provided in the middle of the flow channel 1Q3, for example. The power generating unit 20 generates power using the working fluid flowing therethrough. The power generating unit 20 includes, for example, a gear motor that is driven by the working fluid to generate power. The gear motor includes a pump and a motor connected to the pump. The pump can be a trochoidal pump with trochoidal gears, or a gear pump such as external and elliptic gear pumps. In the gear motor, the speed of the rotation of the pump is increased, so that the motor can generate a large electromotive force. (If a gear pump is employed in the power generating unit 20, a large torque can be produced even if the power generating unit 20 is reduced in size and a large hydraulic resistance can be generated.) In the above manner, the gear motor can contribute to improve the efficiency of the power generation.

The resistance generated in the prosthetic knee joint 1 is determined by the amount of the power to be generated by the power generating unit 20. The amount of the power to be generated is adjusted by changing a power generation resistance, which is generated between the terminals of the gear motor. The power generation resistance is adjusted by performing pulse width modulation (PWM) on a control circuit (not shown) provided between the terminals of the gear motor. The control circuit is constituted by, for example, transistor elements such as FETs connected between the terminals of the gear motor. By performing the PWM to adjust the ON/OFF durations of the transistor elements constituting the control circuit, the power generation resistance generated in the power generating unit 20 is adjusted.

The control unit 1E controls the value of the resistance generated in the fluid circuit 1Q and adjusts the amount of the power generated by the power generating unit 20. The flow rate of the working fluid depends on the speed of the bending and stretching of the knee and thus cannot be directly controlled. The control unit 1E adjusts the relation between the flow rate of the working fluid flowing through the fluid circuit 1Q and the differential pressure (pressure drop) by adjusting the control valves and the power generating unit 20, in order to adjust the resistance generated in the prosthetic knee joint as desired. The control unit 1E controls the stretching-side valve 1G (first parallel control valve) or the bending-side valve 1H (second parallel control valve) independently, to adjust the flow rate of the working fluid in the flow direction toward the power generating unit 20. Here, the differential pressure is calculated as the result of the expression: a valve-dependent constant×flow rate^α, where α is theoretically 2. The control unit 1E adjusts the relation between the flow rate of the working fluid flowing through the fluid circuit 1Q and the differential pressure by, for example, performing the PWM control on the ON/OFF durations of the control circuit connected between the terminals of the gear motor in the power generating unit 20. The control unit 1E controls the control valves in addition to the power generation resistance generated in the power generating unit 20, so that the control unit 1E can adjust the resistance generated in the prosthetic knee joint 1.

Since the gear motor is provided in the power generating unit 20, a large torque can be produced even if the power generating unit 20 is reduced in size. Accordingly, the prosthetic knee joint 1 can generate a large hydraulic resistance. As the prosthetic knee joint 1 has a gear motor; the gear can increase the speed of the rotation of the gear pump if is rotates at low speeds. As a result, the motor can rotate at high speeds, so that an electromotive force can be generated and regenerative power can be obtained. In addition, generating the regenerative power; the prosthetic knee joint 1 can generate a large hydraulic drag force in the gear pump. The prosthetic knee joint 1 can generate power using the resistance experienced by the working fluid, which flows through the fluid circuit operating in response to bending or stretching.

Since the control valves are connected to the power generating unit 20, the prosthetic knee joint 1 can adjust the power generation resistance generated in the power generating unit 20 in a desired manner. Since different flow channels and different control valves are provided in parallel with the power generating unit 20, the prosthetic knee joint 1 can generate a resistance weaker than the power generation resistance generated in the power generating unit 20. According to the prosthetic knee joint 1, the power generation resistance generated in the power generating unit 20 can be adjusted by turning on/of the connection between the terminals of the gear motor. Since different flow channels and different control valves are provided in the prosthetic knee joint 1, the generated resistance can be weaker than can be obtained by the adjustment accomplished by the gear motor.

The power generating unit 20 may use the power generated by the power generating unit 20 to operate or to charge the battery 1J. The fluid circuit 1Q has control valves the stretching-side valve 1G and the bending-side valve 1H) controllable by the control unit 1E. The stretching-side valve 1G and the bending-side valve 1H are parallel control valves respectively connected to the flow channel 1Q1 (a first power generation flow channel) and the flow channel 1Q2 (a second power generation flow channel), which are provided in parallel with the flow channel 1Q The parallel control valves each generate a resistance weaker than the resistance generated by the power generating, unit 20. The control unit 1E adjust the parallel control valves as desired when it is required to generate a resistance weaker than the resistance R1 generated by the power generating unit 20.

The stretching-side valve 1G (the first parallel control valve) is adjusted to reduce the pressure when stretching takes place (when the first port 1C11 experiences high pressure). The bending-side valve 1H (the second parallel control valve) is adjusted to reduce the pressure when bending takes place (when the second port 1C12 experiences, high pressure). In the flow channel 1Q1, the stretching-side valve 1G is connected in series with the stretching-side check valve 1G1 (a first check valve). The stretching-side check valve 1G1 allows the working fluid to flow in the direction from the first port 1C11 to the second port 1C12 and restrict the working fluid from flowing in the direction from the second portion 1C12 to the first port 1C11. In the flow channel 1Q2, the bending-side valve 1H is connected in series with the bending-side check valve 1H1 (a second check valve). Since the stretching- and bending-side check valves 1G1 and 1H1 are provided, the resistances generated through stretching and bending can be adjusted independently.

The bending-side check valve 1H1 allows the working fluid to flow in the direction from the second port 1C12 to the first port 1C11 and restrict the working fluid from flowing in the direction from the first portion 1C11 to the second port 1C12. The stretching- and bending-side valves 1G and 1H are control valves controllable by the control unit 1E and configured to adjust the relation between the flow rate of the working fluid and the differential pressure caused by the pressure loss to generate a desired resistance. When the stretching-side valve 1G is an electromagnetic valve, the opening of the stretching-side valve 1G is adjusted by controlling the number of times the stretching-side valve 1G is opened or closed. When the stretching-side valve 1G is an electromagnetic control valve, the opening of the stretching-side valve 1G is adjusted by controlling how much the stretching-side valve 1G is opened. When the bending-side valve 1H is an electromagnetic valve, the opening of the bending-side valve 1H is adjusted by controlling the number of times the bending-side valve is opened or closed. When the bending-side valve 1H is an electromagnetic control valve, the opening of the bending-side valve 1H is adjusted by controlling how much the bending-side valve 1H is opened.

In the fluid circuit 1Q, a resistance (R1) determined by the flow rate (I1) of the working fluid is generated in the power generating unit 20, and a resistance (R2) determined by the flow rate (I2) of the working fluid (I2) is generated in the stretching-side valve 1G and the bending-side valve 1H. The combined resistance of the fluid circuit 1Q is expressed in the following manner: R1·R2/(R1+R2). The flow rate (I1) of the working fluid in the power generating unit 20 is expressed as follows: I1=R2/(R1+R2). The amount of the power generated in the power generating unit 20 is expressed as follows: R1·I1=R1·R2/(R1+R2).

In the fluid circuit 1Q when stretching takes place, the bending-side check valve 1H1 restrict the working fluid from flowing into the flow channel 1Q2, so that the working fluid flows through the flow channels 1Q3 and 1Q1 and is delivered in the direction from the first port 1C11 to the second port 1C12. In the fluid circuit 1Q, when bending takes place, the stretching-side check valve 1G1 restricts the working fluid from flowing into the flow channel 1Q1, so that the working fluid flows through the flow channels 1Q3 and 1Q2 and is delivered in the direction from the second port 1C12 to the first port 1C11.

If the stretching-side valve 1G or bending-side valve 1H is fully opened during stretching or bending, for example, the working fluid flows through the flow channel 1Q1 or 1Q2 without experiencing, a resistance in the fluid circuit 1Q, and the fluid circuit 1Q exhibits substantially zero resistance irrespective of the resistance (R1) of the power generating unit 20. In this case, the working fluid does not flow through the flow channel 1Q3, and no power is generated in the power generating unit 20. As for the movement of the prosthetic knee joint L it may be required to reduce the bending resistance for example, in the bending period of the swing phase (to deal with a swift movement). It such is the case, the power generating unit 20 behaves as a resistance. Accordingly, the stretching- or bending-side valve 1G or 1H is fully opened, so that the working fluid can flow through the fluid circuit 1Q while encountering substantially no resistance.

If the flow rate at the stretching- or bending-side valve 1G or 1H is gradually lowered in the fluid circuit 1Q during stretching or bending, the resistance (R2) increases, the flow rate (I1) in the flow channel 1Q3 increases, and the power generating unit 20 resultantly generates power. In other words, the power generating unit 20 generates power using the working fluid flowing in the direction permitted by the stretching- and bending side check valves 1G1 (the first check valve) and 1H1 (the second check valve).

In the fluid circuit 1Q, when the stretching- or bending-side valve 1G or 1H is fully closed, the fluid circuit 1Q exhibits the resistance R1, and the flow rate (I1) of the flow channel 1Q3 causes the power generating unit 20 to generate power. In this case, the movement of the cylinder 1C cannot be locked.

As described above, the prosthetic knee joint 1 makes use of the resistance resulting from either bending or stretching of the knee joint of the body and allows the power generating unit to use the resistance to generate power. The prosthetic knee joint 1 makes use of the energy that is otherwise discarded in the conventional art as it generates a resistance during movement of lower extremity prostheses, specifically, regenerate the energy through the power generation. In this way, the internal power source can be saved from being charged frequently and the internal devices can be powered. According to the prosthetic knee joint 1, the power generated in the prosthetic knee joint 1 determines how the control unit operates. This can reduce the number of times the prosthetic knee joint needs to be charged or eliminate the need of the charging. According to the prosthetic knee joint 1, the energy generated by swinging of the user's leg is regenerated into power, so that the regenerative energy can exceed the power consumption.

Second Embodiment

Figure 5:
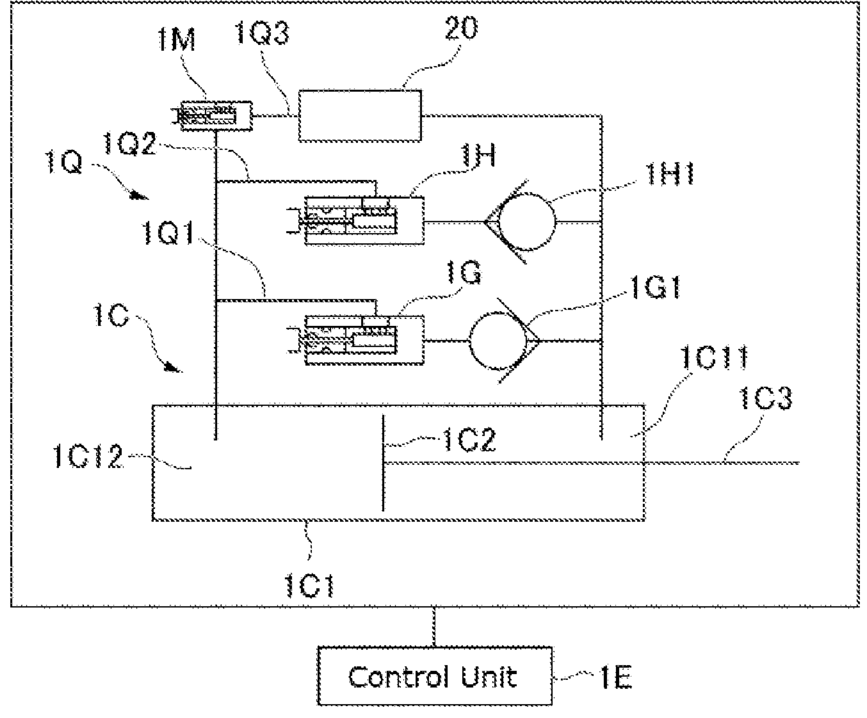
FIG. 5 schematically shows the configuration of a hydraulic circuit relating to a second embodiment.

As, shown in FIG. 5, the fluid circuit 1Q has a first control valve 1M (control valve) in the flow channel 1Q3, and the first control valve 1M is connected in series to the power generating unit 20. The first control valve 1M is provided in the power generation flow channel and configured to control the flow rate of the working fluid flowing through the flow channel 1Q3. The first control valve 1M adds a resistance to the power generating unit 20. As in a fourth embodiment, the control unit 1E controls the stretching-side valve 1G (the first parallel control valve) or the bending-side valve 1H (the second parallel control valve) independently, to adjust the flow rate of the working fluid in the direction toward the power generating unit 20. The control unit 1E adjust the first control valve 1M as desired when it is required to generate a resistance R1 stronger than the resistance R1 generated by the power generating unit 20. The first control valve 1M is connected, for example, in the flow channel 1Q3 between the power generating unit 20 and the second port 1C12. The first control valve 1M may be connected, for example, in the flow channel 1Q3 between the power generating, unit 20 and the first port 1C11.

If the stretching-side valve 1G or the bending-side valve 1H is fully opened during the stretching or bending, for example, the working fluid flows through the flow channel 1Q1 or 1Q2 without experiencing a resistance in the fluid circuit 1Q, and the fluid circuit 1Q exhibits substantially zero resistance irrespective of the resistance (R1) of the power generating unit 20. In this case, the working fluid does not flow through the flow channel 1Q3, and no power is generated in the power generating unit 20. The flow rate at the stretching- or bending-side valve 1G or 1H is gradually lowered in the fluid circuit 1Q during stretching or bending, the resistance (R2) increases, the flow rate (I1) in the flow channel 1Q3 increases, and the power generating unit 20 resultantly generates power.

When the stretching- or bending-side valve 1G or 1H is fully closed and the first control valve I1M is fully closed in the fluid circuit 1Q, the movement of the cylinder 1C can be locked. With the above-described arrangement, the fluid circuit 1Q can, constitute a clutch that is, capable of locking the movement of the prosthetic knee joint 1. In addition, the fluid circuit 1Q can generate a desired resistance force even if the power is turned off and realize a smaller size and a lighter weight.

In order to produce a resistance equal to or greater than the value R1 in the fluid circuit 1Q, the first control valve 1M is fully opened, so that the flow rate (I1) in the flow channel 1Q3 causes the power generating unit 20 to generate power. Accordingly, the resistance (R1) generated in the power generating unit 20 is combined with the resistance (R2) produced by the stretching- or bending-side valve 1G or 1H.

The following describes a method of controlling the fluid circuit 1Q performed by the control unit 1E.

Figure 6:
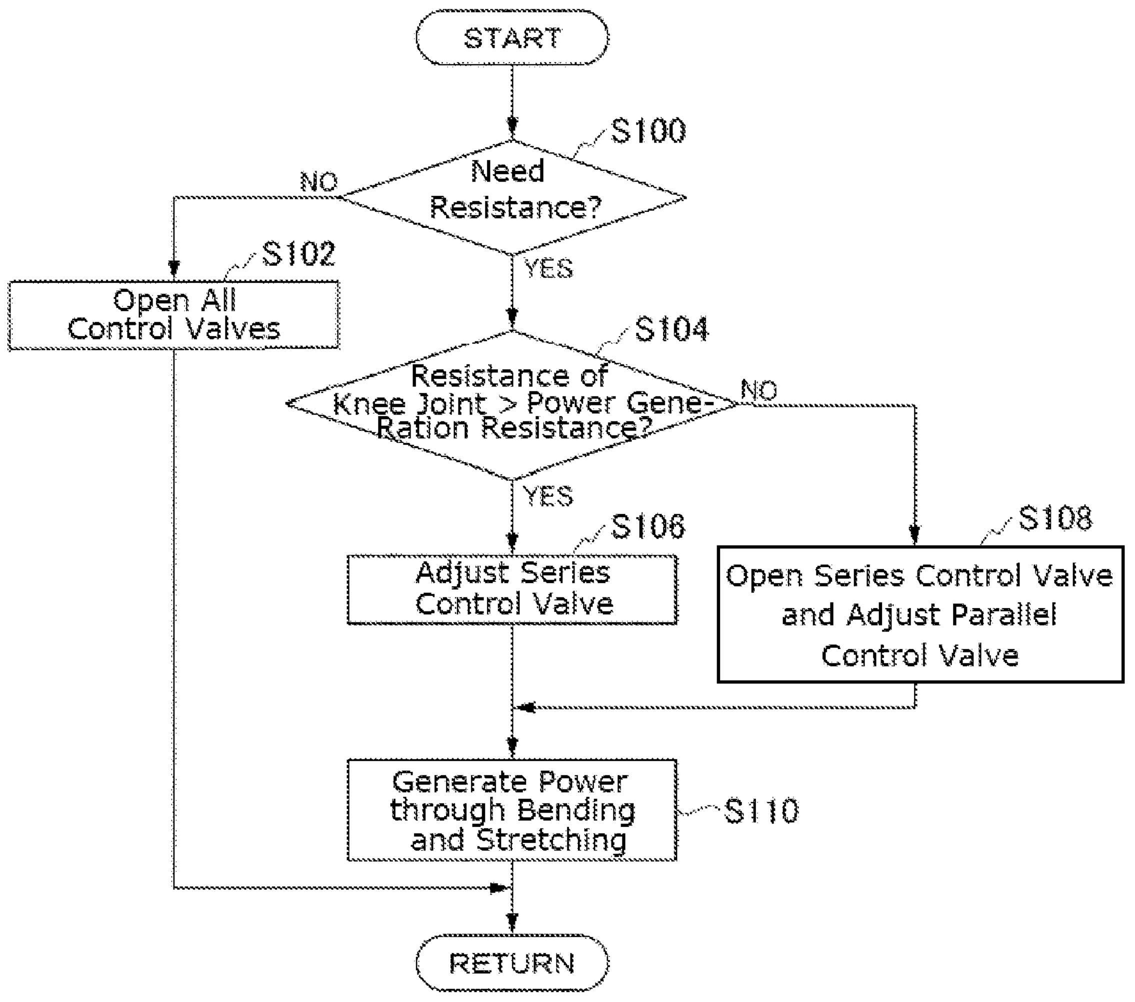
FIG. 6 is a flow chart showing a control method for adjusting a resistance generated in a prosthetic knee joint 1.

FIG. 6 shows a flow of steps included in the method of controlling the fluid circuit 1Q, which is part of the prosthetic knee joint power generation method performed by the control unit 1E. The control unit 1E determines whether or nota resistance is required for stretching or bending of the prosthetic knee joint 1 (Step S100). If no resistance is required (Step S100: No), the control unit 1E fully opens all of the control valves: the first control valve 1M and the stretching- or bending-side valve 1G or 1H (Step S102). If a resistance is required (Step S100: Yes), the control unit 1E determines whether the resistance generated by the prosthetic knee joint 1 is stronger than the power generation resistance generated in the power generating unit 20 (Step S104).

If the required resistance is stronger than the power generation resistance (Step S104: Yes), the control unit 1E fully closes the stretching- or bending-side valve 1G or 1H and adjusts the first control valve 1M (Step S106). If the required resistance is equal to or less than the power generation resistance (Step S104: No), the control unit 1E fully opens the first control valve 1M and adjusts the stretching- or bending-side valve 1G or 1H, which is a parallel control valve (Step S108). The control unit 1E adjusts the control valves and causes the power generating unit 20 to generate power through bending or stretching (Step S110).

As described above, the fluid circuit 1Q relating to the second embodiment can generate a resistance of an appropriate level in the prosthetic knee joint 1, based on the levels of the resistance generated in the prosthetic knee joint 1 and the power generation resistance generated in the power generating unit 20.

In the prosthetic knee joint 1 relating to the second embodiment, the control valve is connected to the power generating unit 20. In this way, the power generation resistance generated in the power generating unit 20 can be adjusted as desired Since different flow channels and different control valves are provided in parallel with the power generating unit 20, the prosthetic knee joint 1 can generate a resistance weaker than the power generation resistance generated in the power generating unit 20. According to the prosthetic knee joint 1, the power generation resistance generated in the power generating unit 20 can be, adjusted by turning on/off the connection between the terminals of the gear motor. Since different flow channels and different control valves are provided in the prosthetic knee joint 1, the generated resistance can be weaker than can be obtained by the adjustment accomplished by the gear motor.

Since the prosthetic knee joint 1 includes the stretching- and bending-side check valves 1G1 (the first check valve) and 1H1 (the second check valve), the prosthetic knee joint 1 can individually adjust the resistances resulting from stretching; and bending. Having the flow channels 1Q1 (the first power generation flow channel) and 1Q2 (the second power generation flow channel), the prosthetic knee joint 1 can generate power using the resistances resulting from stretching and bending.

Third Embodiment

In the fluid circuits 1Q relating to the first and second embodiments, the working fluid, which flows through the power generating unit 20, flows in the reversed direction as the movement of the prosthetic knee joint 1 is switched between bending and stretching. The flow of the working fluid through the power generating unit 20 results in increasing the speed of the rotation of the rotor of the gear motor. This increases the rotational inertia of the rotor part. If the rotor rotates in the forward and reverse directions alternately and this repeatedly occurs, the energy induced by the rotation is lost every time the direction of the rotation changes, which lowers the power generation efficiency. In order to improve the efficiency of power generation done by the power generating unit 20, the working fluid desirably flows in a single direction. According to a third embodiment, the fluid circuit 1Q is configured such that the working fluid flows through the power generating unit 20 in a single direction.

Figure 7:
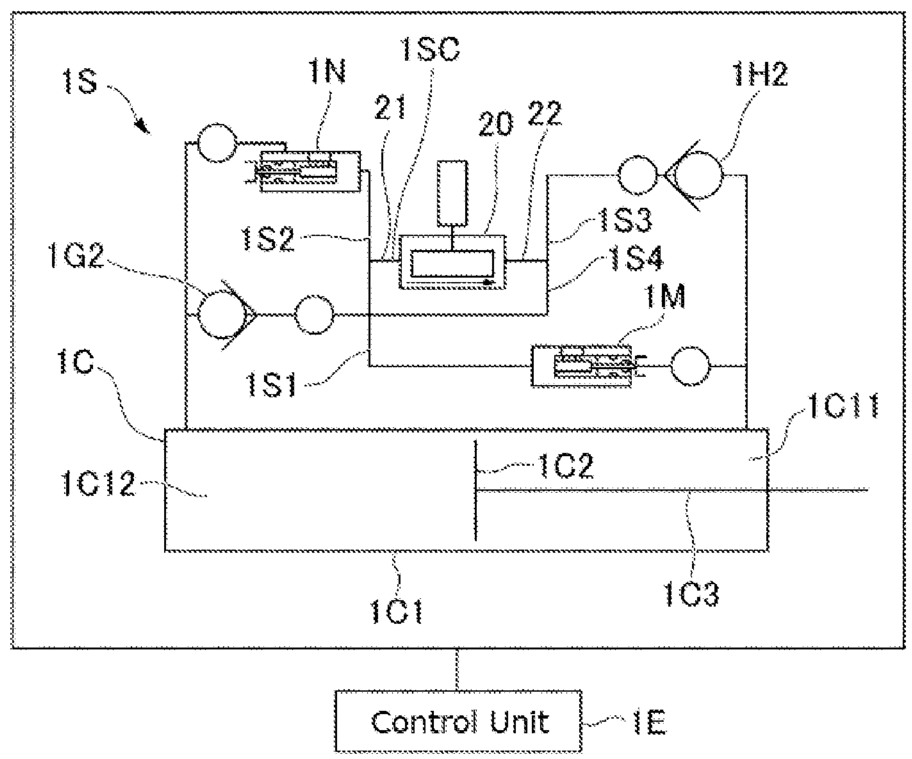
FIG. 7 schematically shows the configuration of a hydraulic circuit relating to a third embodiment.

As shown in FIG. 7, a fluid circuit 1S relating to the third embodiment has a power generation flow channel through which a working fluid flows. The power generation flow channel has an intermediate flow channel 1SC with, a power generating unit 20 being provided in the middle thereof. The intermediate flow channel 1SC has a connecting, part 21 at one end thereof, which is connected to (i) a first flow channel 1S1 connected to the first port 1C11 and (i) a second flow channel 1S2 connected to the second port 1C12. The intermediate flow channel 1SC has a connecting part 22 at the other end thereof, which is connected to (i) a third flow channel 1S3 connected to the first port 1C11 and (i) a fourth flow channel 1S4 connected to the second port 1C12.

The first flow channel 1S1 has a first control valve 1M for adjusting the flow rate of the working fluid. The second flow channel 1S2 has a second control valve 1N for adjusting the flow rate of the working fluid. The third flow channel 1S3 has a third check valve 1H2 for restricting the flow of the working fluid in the direction from the first port 1C11 to the intermediate flow channel 1SC and allowing the flow of the working fluid in the direction from the intermediate flow channel 1SC to the first port 1C11. The fourth flow channel 1S4 has a fourth check valve 1G2 for restricting the flow of the working fluid in the direction from the second port 1C12 to the intermediate flow channel 1SC and allowing the flow of the working fluid in the direction from the intermediate flow channel 1SC to the second port 1C12.

Figure 8:
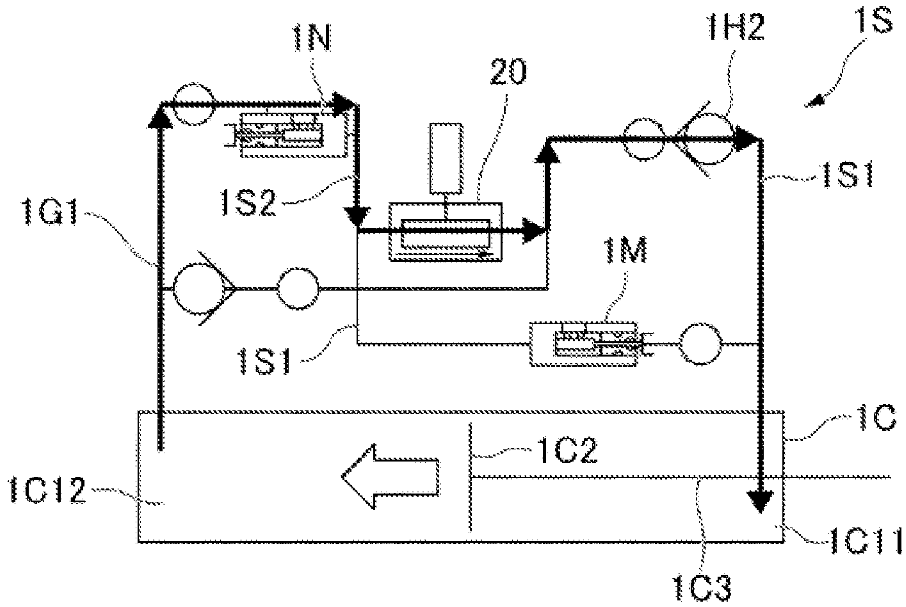
FIG. 8 shows how the hydraulic circuit works during bending.

As shown in FIG. 8, the fluid circuit 1S works in the following manner during bending of the prosthetic knee joint 1. The working fluid is discharged from the second port 1C12, flows through the second control valve 1N, the power generating unit 20, and the third check valve 1H2 and flows into the first port 1C11. In the fluid circuit 1S, the second control valve 1N is controlled so that the resistance of the prosthetic knee joint 1 can be adjusted and power can be generated in the power generating unit 20. Here, since the working fluid also flows through the first control valve 1M, the first control valve 1M may be adjusted to adjust the resistance of the prosthetic knee joint 1.

Figure 9:
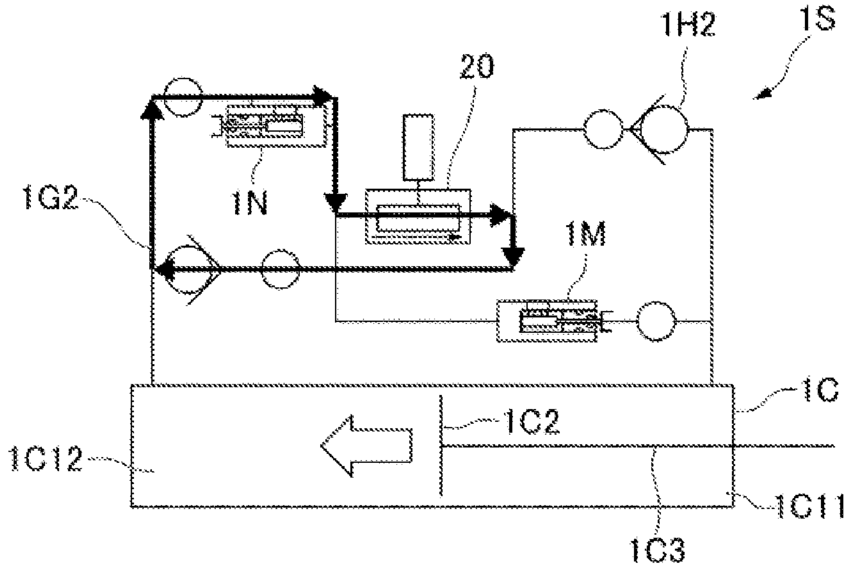
FIG. 9 shows how an idling circuit works when bending slows down and comes to stop.

As shown in FIG. 9, the fluid circuit 1S forms an idling circuit in which the working fluid circulates and flows through the power generating unit 20 when bending of the prosthetic knee joint 1 slows down or comes to stop. The idling circuit is a loop flow channel formed by connecting together the second control valve 1N, the power generating unit 20, and the fourth check valve 1G2. Since the working fluid flows through the idling circuit, the regenerative motor in the power generating, unit 20 is not braked and keeps rotating under the influence of inertia and the power generation continues even if the bending stops. Since the regenerative motor in the power generating unit 20 continues rotating, no energy is lost, due to inertia, so that the power generating unit 20 can generate power in an improved manner.

Figure 10:
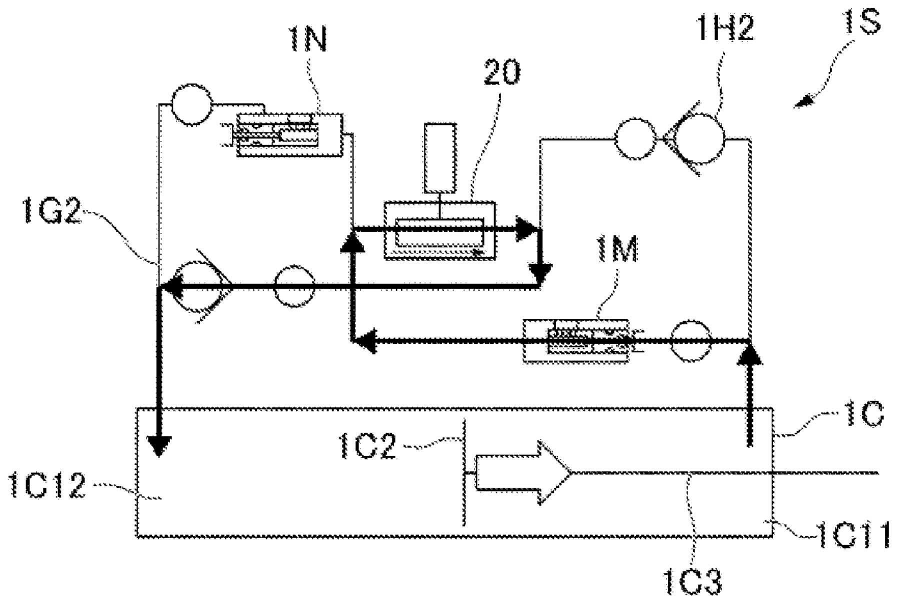
FIG. 10 shows how the hydraulic circuit works during stretching.

As shown in FIG. 10, the fluid circuit 1S works in the following manner during stretching of the prosthetic knee joint 1. The working fluid is discharged from the first port 1C11 in, flows through, the first control valve 1M, the power generating unit 20, and the fourth check valve 1G2 and flows into the second port 1C12. In the fluid circuit 1S, the first control valve 1M is controlled so that the resistance of the prosthetic knee joint 1 can be adjusted and power can be generated in the power generating unit 20. Here, the working fluid flows through the power generating unit 20 in the same direction as during bending. Accordingly, the fluid circuit 1S can achieve improved power generation efficiency when compared with the case where the working fluid flows in the forward and reverse directions through the power generating unit 20.

Since the working fluid flows in a constant direction through the power generating unit 20, the regenerative motor in the power generating unit 20 is not braked and the power generation continues. Since the regenerative motor in the power generating unit 20 continues rotating, no energy is lost due to inertia, so that the efficiency of the power generation improves Since the working fluid also flows through the second control valve 1N, the second control valve 1N may be adjusted to adjust the resistance of the prosthetic knee joint 1.

Figure 11:
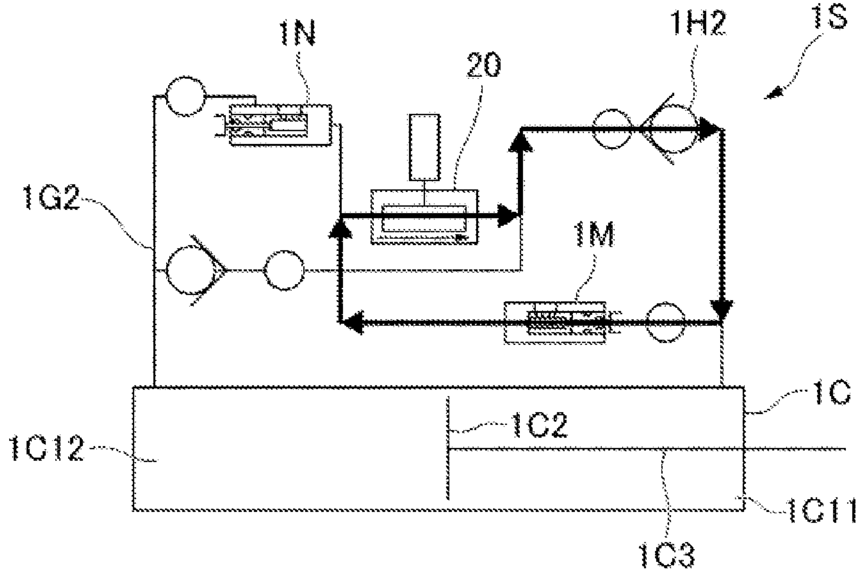
FIG. 11 shows how the idling circuit works when stretching slows down speed and comes to stop.

As shown in FIG. 11, the fluid circuit 1S forms an idling circuit in which the working fluid circulates and flows through the power generating unit 20 when stretching of the prosthetic knee joint 1 slows down or comes to stop.

The idling circuit is a flow channel formed by connecting together the power generating unit 20, the third check valve 1H2 and the first control valve 1M.

Since the working fluid flows through the idling circuit, the regenerative motor in the power generating unit 20 is not braked and the power generating unit 20 continues to, generate power. Since the regenerative motor in the power generating unit 20 continues rotating, no energy is lost due to inertia, so that the power generating unit 20 can generate power in an improved manner.

According to the fluid circuit 1S, during bending, the second control valve 1N serves as a series control valve relative to the power generating unit 20, and the first control valve 1M serves as a parallel control valve relative to the power generating unit 20. During stretching, on the other hand, the first control valve 1M serves as a series control valve relative to the power generating unit 20, and the second control valve 1N serves as a parallel control valve relative to the power generating unit 20. In other words, the fluid circuit 15 behaves in a similar manner as the fluid circuit 1Q relating to the second embodiment (see FIGS. 5 and 6).

According to the prosthetic knee joint 1 relating to the third embodiment, the working fluid can flow in a constant direction through the power generating unit 20 using the resistance generated through stretching or bending. This can reduce the loss in energy in the power generating unit 20 and improve the power generation efficiency.

Fourth Embodiment

Figure 12:
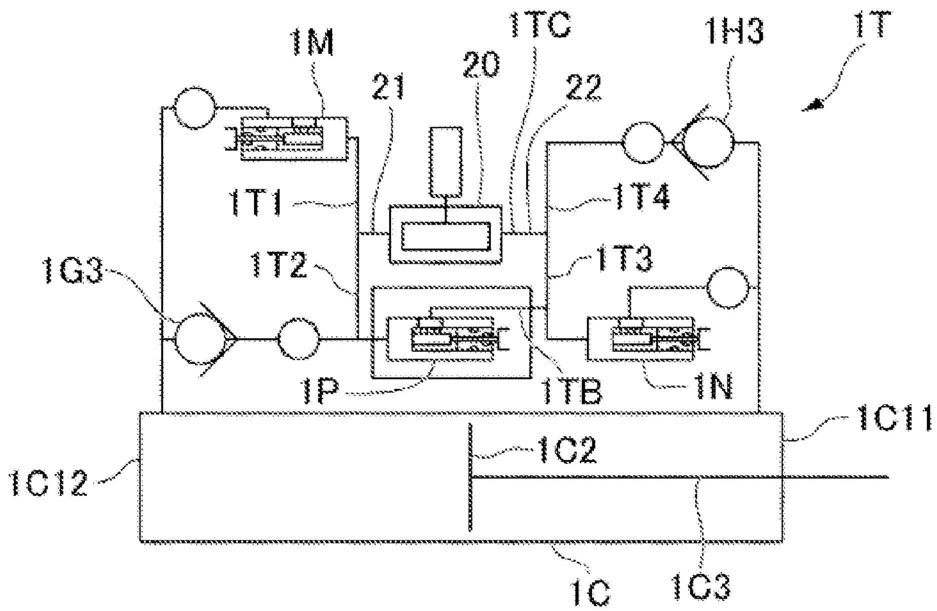
FIG. 12 shows the configuration of a hydraulic circuit relating to a fourth embodiment.

As shown in FIG. 12, a fluid circuit 1T relating to a fourth embodiment forms a power generation flow channel through which the working fluid flows. The power generation flow channel has an intermediate flow channel 1TC with a power generating unit 20 being provided in the middle thereof. The intermediate flow channel 1TC has a connecting part 21 at one end thereof, and the connecting part 21 is connected to a first flow channel 1T1 and a second flow channel 1T2, which are connected to the second port 1C12 and parallel to each other. The intermediate flow channel 1TC has a connecting part 22 at the other end thereof, and the connecting part 22 is connected to a third flow channel 1T3 and a fourth flow channel 1T4, which are connected to the first port 1C11 and parallel to each other. The connecting part 21 at one end of the intermediate flow channel 1TC is connected via a bypass flow channel 1TB to the connecting part 22 at the other end.

The first flow channel 1T1 has a first control valve 1M for adjusting the flow rate of the working fluid. The second flow channel 1T2 has a third check valve 1G3 for allowing the flow of the working fluid from the intermediate flow channel 1TC to the second port 1C12 and restricting the flow of the working fluid from the second port 1C12 to the intermediate flow channel 1TC. The third flow channel 1T3 has a second control valve 1N for adjusting the flow rate of the working fluid. The fourth flow channel 1T4 has a fourth check valve 1H3 for allowing the flow of the working fluid from the intermediate flow channel 1TC to the first port 1C11 and restricting the flow of the working fluid from the first port 1C11 to the intermediate flow channel 1TC. The bypass flow channel 1TB has a bypass control valve 1P for adjusting the flow rate of the working fluid flowing through the bypass flow channel 1TB. The bypass control valve 1P serves as a parallel control valve relative to the intermediate flow channel 1TC of the power generating unit 20.

During bending of the prosthetic knee joint 1, the fluid circuit 1T works such that the working fluid is discharged from the second port 1C12, flows through the first control valve 1M, the power generating unit 20, and the fourth check valve 1H3 and flows into the first, port 1C11. In the fluid circuit 1T, during bending, the first, control valve 1M is controlled so that the resistance of the prosthetic knee joint 1 can be adjusted and power can be generated in the power generating unit 20. Here, since the working fluid also flows through the second control valve 1N, the second control valve 1N maybe adjusted to adjust the resistance of the prosthetic knee joint 1. If the bypass control valve 1P is opened during bending of the prosthetic knee joint 1, the working fluid flows through the bypass flow channel 1TB without going through the power generating unit 20 to flow into the first port 1C11 through the fourth check valve 1H3. Accordingly, no resistance is generated.

In the fluid circuit 1T, the bypass control valve 1P behaves in the same way as the stretching-side valve 1G in the fluid circuit 1Q relating to the second embodiment during stretching, and behaves in the same way as the bending-side valve 1H in the fluid circuit 1Q relating to the second embodiment during bending.

In the fluid circuit 1T, the fourth check valve 1H3 is connected in parallel with the second control valve 1N. Accordingly, if the resistance of the fourth check valve 1H3 is zero during bending of the prosthetic knee joint 1, the overall resistance of the fluid, circuit 1T remains unchanged since the working fluid flows through the fourth flow channel 1T4 irrespective of whether the second control valve 1N is opened or closed Having the fluid circuit 1T relating to the fourth embodiment applied thereto, the prosthetic knee joint 1 can be configured such that bending resistance generated during bending does not depend on whether the second control valve 1N, which is configured to adjust stretching resistance, is opened or closed.

During stretching of the prosthetic knee joint 1, the fluid circuit 1T works such that the working fluid is discharged from the first port 1C11, flows through the second control valve 1N, the power generating unit 20, and the third check valve 1G3 and flows into the second port 1C12. In the fluid circuit 1T, during stretching, the second control valve 1N is controlled so that the resistance of the prosthetic knee joint 1 can be adjusted and power can be generated in the power generating unit 20. Here, since the working fluid also flows through the first control valve 1M, the first control valve 1M may be adjusted to adjust the resistance of the prosthetic knee joint 1. If the bypass control valve 1P is opened during stretching of the prosthetic knee joint 1, the working fluid flows through the bypass flow channel 1TB without going through the power generating unit 20 to flow into the second port 1C12 through the third check valve 1G3. Accordingly, no resistance is generated Irrespective of whether the first control valve 1M is opened or closed, the overall resistance of the fluid circuit 1T remains unchanged.

The bypass control valve 1P is illustrated as a control valve that can be opened or closed by a motor, but the present invention is not limited to such. The bypass control valve 1P may be a bypass relief valve configured to automatically exit the closed state and enter the opened state if the working fluid has a pressure of a predetermined level or more to allow the working fluid to flow therethrough.

According to the prosthetic knee joint 1 of the fourth embodiment, the power generating unit 20 can, generate power using the working fluid that is allowed to flow depending on the resistance generated through stretching or bending. In addition, since the working fluid flows through the first control valve during stretching and through the second control valve during bending, the resistance can be adjusted as desired. The prosthetic knee joint 1 can be controlled to generate no resistance by opening the bypass control valve 1P, which serves as a parallel control valve in the bypass flow channel 1TB.

The prosthetic knee joint 1 can adjust the resistance during bending and stretching independently (as desired) since the working fluid flows through the first control valve during stretching and through the second control valve during bending. In addition, the prosthetic knee joint 1 can be controlled to generate no resistance by opening the parallel control valve in the bypass flow channel. The present invention can generate either a weaker or stronger resistance than the resistance generated in the power generating unit 20.

The control unit 1E described above is implemented by a processor such as a central processing unit (CPU), a graphics processing unit (GPU) executing a program (software). Some or all of the functional parts may be implemented by hardware such as a Large Scale Integration (LSI), an application specific integrated circuit (ASIC) and a field-programmable gate array (FPGA) or by combination of software and hardware cooperating with each other. The program may be stored in advance in a storage device such as a hard disk drive (HDD) or flash memory, or it may be stored in a removable storage medium such as a DVD or CD-ROM and installed in a storage device when the storage medium is connected to a drive device.

The present invention is not limited to the above embodiments but encompasses various modifications of the above embodiments not departing from the purport of the present invention. In the above embodiments, the power generating unit is configured to generate power using a gear motor for example. The present invention, is not limited to such, and the power generating unit may use other power generator devices. For example, the power generating unit may use a linear motor configured to generate power through an extendable and contractable mechanism such as the cylinder in the prosthetic knee joint, or use a regenerative motor provided on the rotation shaft of the prosthetic knee joint. Alternatively, a rack may be formed on the piston rod, and the extension and contraction of the piston rod may be converted into rotation through a pinion gear, the rotation is connected to the gear motor, so that the power generation takes place.

The foregoing embodiments describe members or the like made up by a plurality of parts, and the parts may be combined into a single part. The foregoing embodiments also describe members or the like made up by a single part, and the part may be divided into a plurality of parts. In either case, the members or the like are acceptable as long as they are configured to solve the problems.

According to the foregoing embodiments, a plurality of functions are distributively provided, Some or all of the functions may be integrated. Any one of the functions may be partly or entirely segmented into a plurality of functions, which are distributively provided, Irrespective of whether or not the functions are integrated or distributed they are acceptable as long as they are configured to solve the problems.

What is claimed is:

1. A prosthetic knee joint comprising:

a thigh connection part to be positioned near a thigh part;

a lower leg part rotatably coupled to the thigh connection part;

a power generating unit for generating power using a resistance resulting from rotation of the lower leg part relative to the thigh connection part; and a fluid circuit through which a working fluid flows, the fluid circuit being configured to generate the resistance, wherein the power generating unit generates power through the flowing of the working fluid, wherein the fluid circuit includes a power-generating-unit control valve for adjusting the resistance by controlling the flowing of the working fluid, wherein the prosthetic knee joint further comprises: a control unit for controlling operation of the power-generating-unit control valve, the control unit being configured to operate with the power generated by the power generating unit, wherein the fluid circuit includes:

a hydraulic cylinder configured to operate with the working fluid; and a power generation flow channel connecting together a first port and a second port defined within the hydraulic cylinder and partitioned by a piston movable within the hydraulic cylinder, the power generation flow channel having the power generating unit in a middle thereof, wherein the fluid circuit further includes:

a first parallel flow channel through which the working fluid flows from the first port to the second port, the first parallel flow channel having a first parallel control valve for adjusting a flow rate of the working fluid; and a second parallel flow channel through which the working fluid flows from the second port to the first port, the second parallel flow channel having a second parallel control valve for adjusting a flow rate of the working fluid, wherein the control unit controls the first and second parallel control valves independently, to adjust the flow rate of the working fluid in a flow direction toward the power generating unit, wherein the power-generating-unit control valve connected in series to the power generating unit is provided in the power generation flow channel, and wherein the first parallel flow channel and the second parallel flow channel are provided in parallel with the power generation flow channel, wherein in a case where the working fluid flows from the first port to the second port, when the first parallel control valve is fully opened, the working fluid flows from the first port to the second port through the first parallel flow channel, the working fluid does not flow through the power generation flow channel, and no power is generated in the power generating unit, and when an opening of the first parallel control valve is reduced from when the first parallel control valve is fully opened, the flow rate of the working fluid flowing from the first port to the second port through the first parallel flow channel is lowered and the flow rate of the working fluid flowing from the first port to the second port through the power generation flow channel is increased, compared to when the first parallel control valve is fully opened, and the power generating unit resultantly generates power, and wherein in a case where the working fluid flows from the second port to the first port, when the second parallel control valve is fully opened, the working fluid flows from the second port to the first port through the second parallel flow channel, the working fluid does not flow through the power generation flow channel, and no power is generated in the power generating unit, and when an opening of the second parallel control valve is reduced from when the second parallel control valve is fully opened, the flow rate of the working fluid flowing from the second port to the first port through the second parallel flow channel is lowered and the flow rate of the working fluid flowing from the second port to the first port through the power generation flow channel is increased, compared to when the second parallel control valve is fully opened, and the power generating unit resultantly generates power.

2. The prosthetic knee joint of claim 1, wherein the power generating unit includes a gear motor configured to be driven by the working fluid to generate power.

3. The prosthetic knee joint of claim 1, wherein the power-generating-unit control valve is provided in the power generation flow channel and configured to control a relation between (i) a flow rate of the working fluid flowing through the power generation flow channel and (ii) differential pressure caused by pressure loss.

4. The prosthetic knee joint of claim 3, wherein the first parallel control valve and the second parallel control valve respectively control a relation between a flow rate of the working fluid flowing therethrough and differential pressure caused by pressure loss.

5. The prosthetic knee joint of claim 4, wherein the control unit adjusts a different control valve to generate a resistance weaker than a power generation resistance generated by the power generating unit and adjusts the control valve to generate a resistance stronger than the power generation resistance.

6. The prosthetic knee joint of claim 1, comprising: a first check valve for restricting the working fluid from flowing from the second port to the first port in the first parallel flow channel; and a second check valve for restricting the working fluid from flowing from the first port to the second port in the second parallel flow channel.

7. The prosthetic knee joint of claim 1, wherein the power generation flow channel has:

a first flow channel connecting together the first port and one end of an intermediate flow channel having the power generating unit in a middle thereof;

a second flow channel connecting together the second port and the one end of the intermediate flow channel;

a third flow channel connecting together the first port and the other end of the intermediate flow channel; and a fourth flow channel connecting together the second port and the other end of the intermediate flow channel, wherein the first flow channel has a first control valve for adjusting the flow rate of the working fluid, wherein the second flow channel has a second control valve for adjusting the flow rate of the working fluid, wherein the third flow channel has a third check valve for restricting the working fluid from flowing in a direction from the first port to the intermediate flow channel and allowing the working fluid to flow in a direction from the intermediate flow channel to the first port, and wherein the fourth flow channel has a fourth check valve for restricting the working fluid from flowing in a direction from the second port to the intermediate flow channel and allowing the working fluid to flow in a direction from the intermediate flow channel to the second port.

8. The prosthetic knee joint of claim 1, wherein the power generation flow channel includes:

first and second flow channels parallel to each other and connecting together the second port and one end of an intermediate flow channel having the power generating unit in a middle thereof; and third and fourth flow channels parallel to each other and connecting together the first port and the other end of the intermediate flow channel, wherein the first flow channel has a first control valve for adjusting the flow rate of the working fluid, wherein the third flow channel has a second control valve for adjusting the flow rate of the working fluid, wherein the second flow channel has a third check valve for allowing the working fluid to flow from the intermediate flow channel to the second port and restricting the working fluid from flowing from the second port to the intermediate flow channel, and wherein the fourth flow channel has a fourth check valve for allowing the working fluid to flow from the intermediate flow channel to the first port and restricting the working fluid from flowing from the first port to the intermediate flow channel.

9. The prosthetic knee joint of claim 8, further comprising:

a bypass flow channel connecting together the one end and the other end of the intermediate flow channel; and a bypass control or relief valve provided in the bypass flow channel, the bypass control or relief valve being configured to adjust the flow rate of the working fluid flowing through the bypass flow channel.

10. A prosthetic knee joint power generating method comprising providing the prosthetic knee joint comprising:

a thigh connection part to be positioned near a thigh part;

a lower leg part rotatably coupled to the thigh connection part;

a power generating unit for generating power using a resistance resulting from rotation of the lower leg part relative to the thigh connection part;

and a fluid circuit through which a working fluid flows, the fluid circuit being configured to generate the resistance, wherein the power generating unit generates power through the flowing of the working fluid, wherein the fluid circuit includes a power-generating-unit control valve for adjusting the resistance by controlling the flowing of the working fluid, wherein the prosthetic knee joint further comprises:

a control unit for controlling operation of the power-generating-unit control valve, the control unit being configured to operate with the power generated by the power generating unit, wherein the fluid circuit includes:

a hydraulic cylinder configured to operate with the working fluid;

and a power generation flow channel connecting together a first port and a second port defined within the hydraulic cylinder and partitioned by a piston movable within the hydraulic cylinder, the power generation flow channel having the power generating unit in a middle thereof, wherein the fluid circuit further includes:

a first parallel flow channel through which the working fluid flows from the first port to the second port, the first parallel flow channel having a first parallel control valve for adjusting a flow rate of the working fluid;

and a second parallel flow channel through which the working fluid flows from the second port to the first port, the second parallel flow channel having a second parallel control valve for adjusting a flow rate of the working fluid, wherein the control unit controls the first and second parallel control valves independently, to adjust the flow rate of the working fluid in a flow direction toward the power generating unit, wherein the power-generating-unit control valve connected in series to the power generating unit is provided in the power generation flow channel, and wherein the first parallel flow channel and the second parallel flow channel are provided in parallel with the power generation flow channel wherein in a case where the working fluid flows from the first port to the second port, when the first parallel control valve is fully opened, the working fluid flows from the first port to the second port through the first parallel flow channel, the working fluid does not flow through the power generation flow channel, and no power is generated in the power generating unit, and when an opening of the first parallel control valve is reduced from when the first parallel control valve is fully opened, the flow rate of the working fluid flowing from the first port to the second port through the first parallel flow channel is lowered and the flow rate of the working fluid flowing from the first port to the second port through the power generation flow channel is increased, compared to when the first parallel control valve is fully opened, and the power generating unit resultantly generates power, and wherein in a case where the working fluid flows from the second port to the first port, when the second parallel control valve is fully opened, the working fluid flows from the second port to the first port through the second parallel flow channel, the working fluid does not flow through the power generation flow channel, and no power is generated in the power generating unit, and when an opening of the second parallel control valve is reduced from when the second parallel control valve is fully opened, the flow rate of the working fluid flowing from the second port to the first port through the second parallel flow channel is lowered and the flow rate of the working fluid flowing from the second port to the first port through the power generation flow channel is increased, compared to when the second parallel control valve is fully opened, and the power generating unit resultantly generates power;

wherein the power is generated using the resistance resulting from rotation of the lower leg part relative to the thigh connection part.

11. A prosthetic knee joint comprising:

a thigh connection part to be positioned near a thigh part;

a lower leg part rotatably coupled to the thigh connection part;

a power generating unit for generating power using a resistance resulting from rotation of the lower leg part relative to the thigh connection part;

and a fluid circuit through which a working fluid flows, the fluid circuit being configured to generate the resistance, wherein the power generating unit generates power through the flowing of the working fluid, wherein the fluid circuit includes a power-generating-unit control valve for adjusting the resistance by controlling the flowing of the working fluid, wherein the prosthetic knee joint further comprises:

a control unit for controlling operation of the power-generating-unit control valve, the control unit being configured to operate with the power generated by the power generating unit, wherein the fluid circuit includes:

a hydraulic cylinder configured to operate with the working fluid;

and a power generation flow channel connecting together a first port and a second port defined within the hydraulic cylinder and partitioned by a piston movable within the hydraulic cylinder, the power generation flow channel having the power generating unit in a middle thereof, wherein the fluid circuit further includes:

a first parallel flow channel through which the working fluid flows from the first port to the second port, the first parallel flow channel having a first parallel control valve for adjusting a flow rate of the working fluid;

and a second parallel flow channel through which the working fluid flows from the second port to the first port, the second parallel flow channel having a second parallel control valve for adjusting a flow rate of the working fluid, wherein the control unit controls the first and second parallel control valves independently, to adjust the flow rate of the working fluid in a flow direction toward the power generating unit, wherein the power-generating-unit control valve connected in series to the power generating unit is provided in the power generation flow channel, and wherein the first parallel flow channel and the second parallel flow channel are provided in parallel with the power generation flow channel wherein in a case where the working fluid flows from the first port to the second port, when the first parallel control valve is fully opened, the working fluid flows from the first port to the second port through the first parallel flow channel, the working fluid does not flow through the power generation flow channel, and no power is generated in the power generating unit, and when an opening of the first parallel control valve is reduced from when the first parallel control valve is fully opened, the flow rate of the working fluid flowing from the first port to the second port through the first parallel flow channel is lowered and the flow rate of the working fluid flowing from the first port to the second port through the power generation flow channel is increased, compared to when the first parallel control valve is fully opened, and the power generating unit resultantly generates power, and wherein in a case where the working fluid flows from the second port to the first port, when the second parallel control valve is fully opened, the working fluid flows from the second port to the first port through the second parallel flow channel, the working fluid does not flow through the power generation flow channel, and no power is generated in the power generating unit, and when an opening of the second parallel control valve is reduced from when the second parallel control valve is fully opened, the flow rate of the working fluid flowing from the second port to the first port through the second parallel flow channel is lowered and the flow rate of the working fluid flowing from the second port to the first port through the power generation flow channel is increased, compared to when the second parallel control valve is fully opened, and the power generating unit resultantly generates power and a tangible non-transitory computer-readable storage medium storing a program for generating the power, in the prosthetic knee joint while causing the control unit to control a value of the resistance resulting from rotation of the lower leg part relative to the thigh connection part.

* * * * *